(12) United States Patent
Harttig

(10) Patent No.: US 10,080,497 B2
(45) Date of Patent: Sep. 25, 2018

(54) DEVICE FOR MONITORING AT LEAST ONE BODY FUNCTION OF A USER AND METHOD FOR MANUFACTURING THE SAME

(71) Applicant: Roche Diagnostics Operations, Inc., Indianapolis, IN (US)

(72) Inventor: Herbert Harttig, Neustadt (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 900 days.

(21) Appl. No.: 13/927,487

(22) Filed: Jun. 26, 2013

(65) Prior Publication Data

US 2014/0005492 A1  Jan. 2, 2014

(30) Foreign Application Priority Data

Jun. 28, 2012 (EP) .................................... 12174113

(51) Int. Cl.
| | |
|---|---|
| *A61B 5/1486* | (2006.01) |
| *A61B 5/1473* | (2006.01) |
| *A61B 5/00* | (2006.01) |
| A61B 5/145 | (2006.01) |

(52) U.S. Cl.
CPC ............ *A61B 5/00* (2013.01); *A61B 5/14735* (2013.01); *A61B 5/14865* (2013.01); *A61B 5/6849* (2013.01); *A61B 5/1473* (2013.01); *A61B 5/14503* (2013.01); *A61B 5/14532* (2013.01); *A61B 2562/12* (2013.01); *Y10T 156/10* (2015.01)

(58) Field of Classification Search
CPC .............. A61B 5/14503; A61B 5/1473; A61B 5/14735; A61B 5/14865; A61B 2562/12

USPC ......................................................... 156/295
See application file for complete search history.

(56) References Cited

U.S. PATENT DOCUMENTS

| | | |
|---|---|---|
| 5,413,690 A | 5/1995 | Kost et al. |
| 5,762,770 A | 6/1998 | Pritchard et al. |
| 5,798,031 A | 8/1998 | Charlton et al. |
| (Continued) | | |

FOREIGN PATENT DOCUMENTS

| | | |
|---|---|---|
| EP | 0995784 A1 | 4/2000 |
| EP | 0995784 B1 | 4/2000 |
| (Continued) | | |

OTHER PUBLICATIONS

Adams, R.D. Adhesive Bonding—Science, Technology and Applications. © 2005 Woodhead Publishing.*

*Primary Examiner* — Carson Gross

(74) *Attorney, Agent, or Firm* — Roche Diabetes Care, Inc.

(57) ABSTRACT

A method for manufacturing a device for monitoring at least one body function of a user comprising providing an evaluation unit, providing a sensor unit, aligning a connector portion of the sensor unit next to an electric contact pad of the evaluation unit such that the connector portion faces the electric contact pad, providing at least one anisotropic conductive adhesive between the electric contact pad and the connector portion, and bonding the evaluation unit substrate and the connector substrate together, wherein the electric contact pad and the connector portion are pressed together, and wherein an electric connection of the electric contact pad and the connector portion is created via the anisotropic conductive adhesive.

11 Claims, 3 Drawing Sheets

(56) References Cited

U.S. PATENT DOCUMENTS

| | | | |
|---|---|---|---|
| 5,997,817 A | 12/1999 | Crismore et al. | |
| 6,004,441 A | 12/1999 | Fujiwara et al. | |
| 6,238,597 B1 | 5/2001 | Yim et al. | |
| 6,309,526 B1 | 10/2001 | Fujiwara et al. | |
| 6,360,888 B1* | 3/2002 | McIvor | A61B 5/14532 206/305 |
| 7,527,716 B2 | 5/2009 | Harding | |
| 2008/0086041 A1 | 4/2008 | Heller et al. | |
| 2008/0242962 A1 | 10/2008 | Roesicke et al. | |
| 2008/0275326 A1* | 11/2008 | Kasielke | A61B 5/14865 600/373 |
| 2009/0020502 A1 | 1/2009 | Bhullar et al. | |
| 2010/0094110 A1* | 4/2010 | Heller | A61B 5/14532 600/345 |
| 2011/0000785 A1* | 1/2011 | Bhullar | G01N 33/5438 204/403.01 |

FOREIGN PATENT DOCUMENTS

| | | |
|---|---|---|
| EP | 1152239 A1 | 11/2001 |
| EP | 1987761 A1 | 11/2008 |
| JP | 08138774 A * | 5/1996 |
| KR | 1020110121662 A | 8/2011 |
| WO | 0073785 A2 | 12/2000 |
| WO | 0136953 A1 | 5/2001 |
| WO | 0175438 A3 | 10/2001 |
| WO | 2008131963 A1 | 11/2008 |
| WO | 2009056299 A1 | 7/2009 |

* cited by examiner

DEVICE FOR MONITORING AT LEAST ONE BODY FUNCTION OF A USER AND METHOD FOR MANUFACTURING THE SAME

CROSS-REFERENCES TO RELATED APPLICATION(S)

This application claims priority to European patent application no. 12174113.6 which was filed on Jun. 28, 2012.

FIELD OF THE INVENTION

The invention generally relates to a method for manufacturing a device for monitoring at least one body function of a user. The invention further relates to a device for monitoring at least one body function of a user, which, preferably, is obtainable by using the method according to the invention. However, other methods of manufacturing are feasible. Methods and devices according to the present invention mainly are used in any field of monitoring one or more body functions, such as for monitoring a physiological state of a body of a user, and, more preferably, for monitoring an analyte concentration in a body fluid of the user and/or for monitoring one or more other types of body functions, such as a heart rate, a blood pressure or other types of body functions. Preferably, the device according to the present invention may be used for in vivo measurements of an analyte concentration in a body fluid of a user. However, other fields of application are possible.

DESCRIPTION OF THE RELATED ART

In the field of medical technology, specifically in the field of monitoring health conditions of patients in hospitals or in the field of home monitoring, a large number of devices for measuring one or more parameters related to one or more body functions is known. Thus, specifically, sensor elements for measuring heart rates, blood pressure or concentrations of one or more analytes in a body fluid of the user are known. In the following, without restricting the scope of the present invention and without restricting the possibility of using other types of sensor units, the invention is mainly disclosed in the context of electrochemical sensor units capable of electrochemically measuring the concentration of one or more analytes in a body fluid, such as for measuring glucose in blood and/or interstitial fluid.

Thus, electrochemical tests are known, which are also referred to as electrochemical biosensors. Biosensors of this type mainly are used for qualitatively and/or quantitatively analyzing the content of biological liquids such as blood, plasma, interstitial fluid (ISF) or urine. The analyte which is most widely detected in the art is glucose. However, additionally or alternatively, detectors for other types of analytes are known, such as detectors for detecting lactate, PTT (partial thromboplastin), a pH value, urea, lipids, ethanol, cholesterol or other types of analytes. Examples for specific embodiments of electrochemical glucose sensor units are disclosed in U.S. Pat. No. 5,413,690, U.S. Pat. No. 5,762,770, U.S. Pat. No. 5,798,031, U.S. Pat. No. 5,997,817, US 2009/0020502 and WO 2009/056299.

In the art, for analyzing body fluids, so-called spot measurements are known, which require a sampling of a specific sample of a body fluid, which, subsequently, is analyzed by using a measurement device or sensor unit. Further, besides spot measurements, continuous measurements are known. Thus, specifically in the field of glucose measurement in the interstitial body tissue (interstitium), continuous measurement methods and devices are known, which are also referred to as CM devices. These continuous monitoring methods and devices are specifically useful for managing, monitoring and controlling specific types of illnesses such as a diabetes status. Meanwhile, implanted electrochemical sensor elements are used, which are also referred to or which may be embodied as so-called needle-type sensors or NTS. Therein, an active sensor portion having one or more electrodes is directly placed in the region of measurement, such as in the interstitial tissue. Further, by using one or more sensor electrodes or working electrodes having at least one detector substance having one or more enzymes, electrochemical in-situ or in-vivo measurements may be performed. Thus, as an example, enzymes such as glucose oxidase may be used, which are adapted for generating an electric charge, an electric current or an electric potential in the presence of glucose, from which the concentration of glucose may be derived and which may be used as a measurement signal or measurement information. Examples of these types of transcutaneous measurement systems are disclosed in U.S. Pat. No. 6,360,888 or in US 2008/0242962 A1.

Generally, continuous monitoring systems as known in the art are transcutaneous systems. As used herein, the term transcutaneous system refers to a device for monitoring the body function, wherein the device comprises a transcutaneous sensor unit. This transcutaneous sensor unit, preferably containing one or more electrodes, is placed beneath the skin of the user in a body tissue of the user. A part of the sensor unit may reach through the skin of the user, in order to be electrically connected to an electronic unit, which is also often referred to as an evaluation unit or patch and which generally may be adapted for controlling the sensor unit and/or for evaluating signals provided by the sensor unit. The evaluation unit generally may be located outside the body of the user, which may be a human or an animal. The device according to the present invention also may optionally be embodied as a transcutaneous system. In transcutaneous systems, generally, the sensor unit is fully or partially inserted into the body tissue by using one or more inserters or insertion aids. Examples of inserters are disclosed in U.S. Pat. No. 6,360,888 B1. Other types of inserters are known. Typically, transcutaneous systems are worn by the user for a time period from several hours to several months or typically several days to several weeks, or, more typically, one week.

Specifically in the field of transcutaneous sensor systems, a large number of technical challenges referring to patterning of the substrates, assembly techniques, electrical contacting and packaging arise. Thus, needle-type sensors which are often used as sensor units for transcutaneous systems, generally require flexible, elongated substrates comprising fine conductive paths having a low electrical resistance. The flexibility of the sensor substrates as well as the requirement of high-definition patterning and reliable contacting of the sensor electrodes imposes a major technical challenge. Further, specifically in view of rising costs in the field of medical technology, cost-efficient manufacturing and assembly techniques are generally required.

In the art of electronics, specifically in the field of semiconductor manufacturing or in the field of manufacturing of integrated circuits (ICs), a large number of manufacturing technologies is generally known. Thus, various printing techniques or patterning techniques are disclosed, such as lithographic techniques or etching techniques. Further, a patterning of conductive paths and electrodes by laser ablation techniques is disclosed in U.S. Pat. No. 6,044,441, in U.S. Pat. No. 6,309,526 B1, in WO 00/73785 A2, in WO 01/36953 A1, in WO 01/754438 A2 and in EP 1 152 239 A1. Further, printing techniques for electrode patterning are known, such as from U.S. Pat. No. 6,004,441. These techniques are generally limited by resolution.

Further, in the field of sensor devices as well as in other technical fields, a large number of contacting techniques is known. As an example, contacting of test strips via connector pins or spring contacts is disclosed in U.S. Pat. No. 7,527,716 B2. Further, in other fields of assembly technology, the use of conductive adhesives is known. Thus, anisotropic conductive adhesives are used for assembly of flip-chip-devices in integrated circuits, such as disclosed in EP 0 995 784 B1 or in U.S. Pat. No. 6,238,597 B1. Further, the use of anisotropic adhesives for contacting conductive polymeric electrodes in touch panel displays is disclosed in US 2012/0032910 A1.

Despite the advantages implied by the techniques listed above, a large number of technical challenges remain in medical technology, specifically for contacting sensor units for monitoring one or more body functions of a user. Specifically, an electrical contacting of fine patterns, specifically conductive paths having a low width, remains a technical challenge. Thus, specifically, needle-type sensors typically require sensor units having an elongated shape with a length of typically several ten millimeters and a width of generally less than 5 mm or even less than 3 mm. Still, reliable conductive paths have to be manufactured, providing a low electrical resistance for precise electrochemical measurements at a high signal-to-noise ratio. Therein, specifically, flexible properties of the sensor unit have to be taken into account. Thus, generally, a mechanical contacting such as by using spring-based electric contacts may lead to interruptions of the contacts or even damaging of the contacts, specifically due to microscopic movements of the spring contacts during use of the device.

It is therefore an objective of the present invention to provide a device for monitoring at least one body function of a user as well as a method for manufacturing the same which fully or partially solve the shortcomings of the above-mentioned known techniques. Specifically, the device and the method shall provide a reliable and cost-effective way of contacting a sensor unit for monitoring one or more body functions, such as by electrically contacting the sensor unit to an evaluation unit. Therein, high-precision electric contacts shall be provided, having a low electrical resistance and, still, having a high robustness against mechanical movements.

BRIEF SUMMARY OF THE INVENTION

It is against the above background that the present invention provides certain unobvious advantages and advancements over the prior art. In particular, the inventors have recognized a need for improvements in a device for monitoring at least one body function of a user as well as by a method for manufacturing a device for monitoring at least one body function of a user, the method and the device having the features of the independent claims. Preferred embodiments, which might be realized in an isolated fashion or in an arbitrary combination, as the skilled person will realize, are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

In a first aspect of the present invention, a method for manufacturing a device for monitoring at least one body function of a user is disclosed. As used herein, the term "body function" may generally refer to an arbitrary measurable parameter of the body of the user, the latter being a human or an animal. The parameter may generally comprise any measurable parameter of the user, such as a parameter indicating a body function or a health state of the user. Thus, one or more medical and/or physiological parameters may be measured, such as one or more of a blood pressure, a heart rate, a temperature, a pH value and a concentration of at least one analyte in at least one body fluid. As further used herein, the term "monitoring" generally may refer to measuring the above-mentioned one or more parameters indicating the body function of the user. Thus, one ore more measurement values may be acquired, preferably a plurality of measurement values at different points in time, such as a measurement curve indicating measurement values as a function of time. The monitoring preferably may be an in-vivo monitoring, as will be outlined in further detail below.

The device preferably may be a compact, wearable or portable device which may be carried by a user, such as a device having a volume of less than 1000 cm$^3$ or even less than 500 cm$^3$, and/or having a weight of less than 500 g, preferably of less than 200 g. Specifically, the device may fully or partially be carried on a body surface of the body of the user.

The device comprises at least one evaluation unit and at least one sensor unit. As used herein, the term evaluation unit refers to a one-component or multi-component element of the device which is adapted for controlling the device and/or which is adapted for acquiring measurement values and, optionally, for fully or partially evaluating the measurement values, acquired by the at least one sensor unit. As further used herein, the term sensor unit generally refers to a one-component or multi-component element of the device which is adapted for measuring the at least one parameter indicating the at least one body function. Thus, the sensor unit, as outlined in further detail below, preferably may comprise one or more electrochemical sensors for electrochemically measuring the concentration of at least one analyte in a body fluid. However, additionally or alternatively, other types of sensor units may be comprised, such one or more of a sensor unit for detecting a heart rate, such as by detecting appropriate movements due to a heartbeat, a blood pressure measurement unit, a temperature sensor, a pH sensor or any other types of sensor units or combinations thereof. As indicated above, the sensor unit preferably is a continuous monitoring sensor unit adapted for acquiring measurement values as a function of time. Preferably, the sensor unit comprises at least one transcutaneous sensor unit having at least one portion implantable through the skin into a tissue of the body. Thus, as outlined above, the sensor unit preferably is a sensor unit adapted for in-vivo measurements, preferably a sensor unit for in-vivo measurements of a concentration of an analyte concentration in a body tissue and/or a body fluid of the user.

The method comprises the following steps. Therein, the method steps may be performed in the given order. However, another order of the method steps is possible. Further, it is possible to perform one or more of the method steps simultaneously or at least partially simultaneously. It is further possible to perform one or more of the method steps repeatedly. Further, the method may comprise additional method steps which are not listed. The comprised method steps are as follows:

a) a step of providing the evaluation unit, wherein the evaluation unit has at least one electric contact pad applied to at least one evaluation unit substrate, wherein the electric contact pad is electrically connected to at least one electronic device of the evaluation unit;

b) a step of providing the sensor unit, wherein the sensor unit comprises at least one connector part, wherein the connector part comprises at least one connector substrate and at least one conductive path applied to the connector substrate, wherein the conductive path comprises at least one electrically conductive material, preferably an electrically conductive organic material, and wherein the conductive path has at least one connector portion;

c) a preparation step, wherein the connector portion is aligned next to the electric contact pad such that the connector portion faces the electric contact pad, wherein at least one anisotropic conductive adhesive is provided in between the electric contact pad and the connector portion;

d) a bonding step, wherein the evaluation unit substrate and the connector substrate are pressed together, wherein the electric contact pad and the connector portion are pressed together, wherein an electric connection of the electric contact pad and the connector portion is created via the anisotropic conductive adhesive.

As used herein, the term providing generally refers to introducing the respective unit or element into the manufacturing method. The step of providing may further comprise fully or partially manufacturing the element to be provided. Additionally or alternatively, commercially available elements may be used or elements manufactured elsewhere or in a separate process.

As outlined above, the evaluation unit has an electric contact pad applied to at least one evaluation unit substrate. As used herein, the term evaluation unit substrate refers to an arbitrary substrate, preferably a plate-shaped substrate, i.e. an element having a lateral extension exceeding its thickness by at least a factor of 10, more preferably at least a factor 20 or more. Preferably, the at least one evaluation unit substrate may comprise at least one printed circuit board, such as a printed circuit board made of a plastic material and/or a ceramic material and/or a metal and/or a paper material. Further, multi-layer setups may be used. However, other types of evaluation unit substrate materials may be feasible. The electric contact pad, as outlined above, may provide a contact surface area, such as an area having a rectangular shape, a polygonal shape or a round shape. Preferably, the one or more electric contact pads are fully or partially made of a metallic material. Thus, the one or more electric contact pads may comprise at least one gold layer. In addition or alternatively, other types of metal layers may be applied, such as at least one of: Cu, Ni, Ag, Au, Pd, Pt. Again, additionally or alternatively, the at least one electric contact pad may fully or partially be made of at least one non-metallic electrically conductive material, such at least one of: a conductive carbon material, such as graphite, graphene, carbon nanotubes, glassy carbon; an electrically conductive organic material, such as an electrically conductive polymer.

The evaluation unit substrate may comprise a plurality of electric leads or paths, wherein at least one of these leads or paths leads to the electric contact path applied to the evaluation unit substrate. Additionally or alternatively, at least one electric via may be present in the evaluation unit substrate, in order to electrically contact the electric contact pad.

The electric contact pad is electrically connected to at least one electronic device of the evaluation unit. This connection may be made through the above-mentioned at least one wire, path or via. The at least one electronic device preferably may comprise at least one semiconductor device, preferably at least one active semiconductor device, such as an amplifier and/or an integrated circuit. Additionally or alternatively, the at least one electronic device may comprise at least one application-specific integrated circuit (ASIC). For further potential details of evaluation units for evaluating electrochemical measurements, reference may be made to the prior art mentioned above, such as to the setup of the base station in US 2008/0242962 A1 having one or more electronic components such as one or more potentiostats and/or other types of electronic components. Thus, preferably, the at least one electronic device of the evaluation unit electrically connected to the at least one electric contact pad preferably may comprise at least one potentiostat, i.e. an electronic device used in electrochemical measurements which may provide a precise D.C. voltage source and/or which may act as a high-precision voltmeter or ammeter, preferably a voltmeter or ammeter having a high impedance. The potentiostat may further be adapted to act as a high-precision amplifier. Examples of potentiostats of this type are widely known in the art. Additionally or alternatively, the at least one electronic device may comprise other types of electronic components.

As outlined above, the sensor unit comprises at least one connector part having at least one connector substrate. The connector part may be an arbitrary element of the sensor unit adapted for electrically connecting a sensor element, a sensor region or any other component of the sensor unit to the evaluation unit. As outlined in further detail below, the connector part preferably may have an elongated shape. As used herein, the term connector substrate may refer to an arbitrary substrate adapted for carrying one or more components of the sensor unit and for connecting the above-mentioned sensor element or sensor part of the sensor unit to the electronic device. Most preferably, the connector substrate may comprise at least one plastic substrate such as a printed circuit board and/or a flexible connector. Additionally or alternatively, other types of substrate materials may be used, in a single-layer setup or in a multi-layer setup, such as one or more of the following materials: a plastic material, a paper material, a metal, a ceramic material. The connector substrate preferably may be a flexible connector substrate, i.e. a substrate which, by manual force, may be bent. Thus, the connector substrate may comprise a so-called flex connector. Preferably, the at least one connector substrate may comprise at least one plastic film or plastic foil.

As outlined above, the connector part further comprises at least one conductive path applied to the connector substrate, the conductive path comprising at least one electrically conductive material having at least one connector portion. Preferably, the electrically conductive material comprises at least one electrically conductive polymer. However, additionally or alternatively, other electrically conductive materials may be used, such as electrically conductive carbon materials and/or metals, as will be outlined in further detail below.

As used herein, the term conductive path refers to an electric lead applied to the connector substrate, wherein the lead is defined by one or more conductive layers applied to the connect- or substrate. As used herein, the term conductive generally refers to materials having an electric conductivity of at least 0.001 S/cm, more preferably at least 0.01 S/cm and most preferably at least 0.1 S/cm. The conductive path preferably may have an elongated shape, i.e. a length along the connector substrate exceeding a width in a plane of the connector substrate by at least a factor of 10, more preferably by at least a factor 100.

The electrically conductive material preferably may be a material or may comprise one or more materials selected from the group consisting of: an electrically conductive organic material, preferably at least one electrically conductive polymer; an electrically conductive carbon material, preferably one or more of graphite, graphene, glassy carbon and carbon nanotubes; a metal, preferably a metal selected from the group consisting of Cu, Ni, Ag, Au, Pd and Pt. However, additionally or alternatively, one or more other electrically conductive materials may be used.

As further used herein, the term electrically conductive organic material may refer to an arbitrary organic material having electrically conductive properties as defined above. Thus, the at least one organic material may comprise at least one organic film. Thus, a polymer material may be comprised or any other organic material, such as a monomeric organic material or a polymeric organic material, having electrically conductive properties.

Electrically conductive materials and, more specifically, electrically conductive organic materials such as electrically conductive polymers are widely known in the art. Thus, electric conductivity in organic materials may be generated by introducing appropriate dopant materials, such as electrically conductive particles and/or dopants creating dislocated or movable electric charges. Most preferably, however, the electrically conductive organic material is or comprises an intrinsically conductive organic material, i.e. an organic material having molecular structures capable of providing a charge transport and/or charge dislocation, such as by using a dislocated electron system. Typically, the electrically conductive organic material may comprise an organic material having an extended π-electron system, such as by providing a plurality of conjugated double bonds. Ideally, the electrically conductive organic material is capable of reversibly being oxidized and/or reduced by electrochemical means, i.e. by designing the electrically conductive organic material such that the electrically conductive material may form stable cations or anions.

As further used herein, the term connector portion refers to an arbitrary part of the conductive path adapted for being connected to the electric contact pad. Thus, the connector portion may be formed by an exposed portion of the conductive path, such as a portion having a round or rectangular shape or any other arbitrary shape, preferably a portion having a dimension (such as a width perpendicular to a lateral extension of the conductive path) which is wider than the remaining conductive path. Similarly, the electric contact pad may have a round, a rectangular or a generally an arbitrary shape. Both the connector portion and the contact pad may thus provide exposed conductive surface areas. Since, as outlined in further detail below, the connector portion will be connected to the electric contact pad, the connector portion and the electric contact pad preferably have similar or compatible surface geometries. Thus, preferably, a surface area of the electric contact pad and a surface area of the connector portion provide a substantially identical surface area, wherein the term substantially may include slight deviations of an identical surface area, such as deviations of preferably less than 50%, more preferably less than 20%. Both the connector portion and the contact pad may have a similar or identical geometric shape. Thus, both the connector portion and the electric contact pad may provide a rectangular shape, preferably a rectangular shape of the same or substantially the same width, wherein the term substantially may include slight deviations of an identical width, such as deviations of preferably less than 50%, more preferably less than 20%. Other geometric shapes are possible.

As outlined above, the connector portion, in the preparation step, is aligned next to the electric contact pad such that the connector portion faces the electric contact pad. Most preferably, as outlined in further detail below, a plurality of electric contact pads and a plurality of connector portions are provided. In this case, the alignment preferably takes place such that corresponding electric contact pads and corresponding connector portions are aligned facing each other. Thus, one or more specific electric contact pads out of the plurality of electric contact pads may be aligned facing one or more specific corresponding connector portions out of the plurality of connector portions. Thus, preferably, a 1:1 correspondence may be provided, such that one specific electric contact pad is aligned facing one specific corresponding connector portion. However, other embodiments are feasible, such as a 2:1 or a 1:2 correspondence or other embodiments.

Further, as outlined above, at least one anisotropic conductive adhesive is provided in between the electric contact pad and the connector portion. As used herein, the term anisotropic conductive adhesive generally may refer to an adhesive material or adhesive element which, per se and/or after appropriate treatment (such as by applying pressure and/or heat) provides anisotropic conductive properties. Thus, preferably, the anisotropic conductive adhesive has electrically conductive properties in a direction pointing from the electric contact pad to the connector portion or vice versa, and has electrically insulating properties in a direction perpendicular to said direction, preferably in an arbitrary direction perpendicular to the connection between the electric contact pad and the connector portion. As used herein, the term electrically insulating refers to a material having an electric conductivity below 0.001 S/cm, preferably below 0.0001 S/cm, most preferably below $10^{-6}$ S/cm, even more preferably below $10^{-8}$ S/cm, below $10^{-9}$ S/cm, below $10^{-10}$ S/cm or even below $10^{-11}$ S/cm.

Anisotropic conductive adhesives are known in the art and are commercially available. Thus, as outlined above, reference may be made to US 2012/0032910 A1. Anisotropic conductive adhesives are generally used in the field of display manufacturing for providing electrical and mechanical connections from driver electronics to glass substrates of liquid crystal displays. Generally, anisotropic conductive materials may provide one or more adhesive compounds as a matrix or adhesive material. As an example, the matrix material or adhesive material may comprise an epoxy resin and/or an acrylate resin. Generally, the matrix material may comprise a curable material, such as a thermosetting material and/or a photochemically setting material. Further, the anisotropic conductive adhesive may comprise one or more conductive components, such as one or more electrically conductive particles. Anisotropic conductive adhesives are commercially available, such as by Sony Chemicals and Information Devices, Nippon Graphite Industries, Hitachi Chemicals or Panacol-Elosol GmbH, Germany.

In order to provide the at last one anisotropic conductive adhesive, wherein a one-component or multi-component anisotropic conductive adhesive may be used, several techniques are possible. Thus, the anisotropic conductive adhesive may be applied to the electric contact pad or to the connector portion or both. The at least one anisotropic conductive adhesive may be provided as a film and/or in an amorphous form, such as in a liquid form or as a paste. Additionally or alternatively, the at least one anisotropic conductive adhesive may be provided and/or applied as a film. Preferably, the at least one anisotropic conductive adhesive is provided in a deformable form, followed by one or more hardening steps, such as a thermosetting and/or a chemical hardening. Additionally, or alternatively, the at least one anisotropic conductive adhesive may comprise at least one anisotropic conductive film, i.e. a free-standing film-type element which may be applied to the electric contact pad, the connector portion or both.

As outlined in further detail below, in case a plurality of electric contact pads and a plurality of connector portions is provided, the at least one anisotropic conductive material preferably is simultaneously provided for a group of these connector portions and electric contact pads or preferably for all of the connector portions and electric contact pads. Thus, both by applying a film and by applying an amorphous material, a large-area application may be provided, wherein a plurality of the electric contact pads or even all of the electric contact pads and/or a plurality of the connector portions or even all of the connector portions is covered by a common amount of the anisotropic conductive adhesive. As explained above, the anisotropic properties may lead to a connection of corresponding electric contact pads and connector portions, whereas an insulation is provided between neighboring connector portions and/or neighboring electric contact pads.

As outlined above, in the bonding step, the evaluation unit substrate and the connector substrate are pressed together. Therein, a pressure may be applied to the evaluation unit substrate and/or the connector substrate at least in the region of the electric contact pad and/or in the region of the connector portion. Thus, the pressure may be applied locally in the region of the electric connection in between the electric contact pad and the connector portion. For applying the pressure, various tools may be used. Thus, preferably, one or more stamps may be used for locally applying pressure. Most preferably, a pressure of at least 0.5 MPa may be applied, more preferably of at least 1 MPa or even a pressure of more than 1 MPa, such as a pressure of 1-10 MPa. As outlined in further detail below, when pressing the electric contact pad and the connector portion together, one or more of heat, pressure and radiation (such as electromagnetic radiation and/or infrared radiation) may be applied to the anisotropic conductive adhesive in between the electric contact pad and the connector portion. Thus, e.g., heat may be applied through the evaluation unit substrate in the region of the electric contact pad and/or through the connector substrate in the region of the connector portion. Thus, as an example, a temperature of at least 100° C. may be applied by using at least one stamp, such as a temperature of 100° C.-200° C., preferably a temperature of 120° C.-170° C. Further examples will be given below. Generally, the application of pressure in the bonding step may generally be combined with an application of heat and/or radiation, such as by applying pressure and heat or by applying pressure and radiation.

As outlined above, in step d), an electric connection of the electric contact pad and the connector portion is created via the anisotropic conductive adhesive. Thus, in step d), by pressing the electric contact pad and the connector portion together, the anisotropic conductive adhesive in between the connector portion and the electric contact pad is compressed, thereby generally and preferably introducing the anisotropic properties of conductance. Thus, as outlined above, the electric conductivity may be provided in the direction of compression, i.e. in a direction from the electric contact pad to the connector portion or vice versa, whereas electrically insulating properties are provided in an arbitrary perpendicular direction, i.e. in a plane perpendicular to this direction.

Preferably, as outlined above, the sensor unit may comprise at least one implantable sensor unit. The implantable sensor unit comprises at least one implantable portion adapted for implantation into a body tissue of the user. As used herein, the term implantable refers to the fact that the respective element may be inserted into a body tissue of the user. For this purpose, the implantable element may comprise appropriate dimensions, such as an extension in an arbitrary direction of the implantable component of no more than 50 mm, preferably of no more than 30 mm. Most preferably, the implantable element has biocompatible properties, such as by avoiding the use of toxic surface materials. For this purpose, as known in the art, the implantable component may comprise biocompatible materials and/or may be covered by a biocompatible cover, such as by a biocompatible membrane, more preferably a semi-permeable membrane. Thus, the implantable component, such as the implantable portion adapted for implantation into the body tissue, may fully or partially be covered by a semi-permeable membrane allowing for a permeation of the analyte to be detected, such as glucose, and/or for a permeation by an electrolyte such as water, whereas components of the implantable portion such as a detector substance or parts thereof, are held back by the semi-permeable membrane. These types of membranes are known in the art. As an example, polyimide membranes and/or hydrogel membranes may be used, e.g. membranes as disclosed in WO 2007/071562 A1 and/or in WO 2005/078424 A1. However, other types of sensor setups may be used.

Further, in order to further enhance implantability of the implantable portion, the implantable portion may fully or partially be embodied as a flexible implantable portion, i.e. a portion which may easily be reversibly bend by a bending radius of 20 mm or less by applying typical forces occurring during implantation, such as forces of less than 10 N.

The sensor unit may preferably have an elongated shape having a longitudinal extension, such as an extension along an axis of implantation into the body tissue, and a lateral extension perpendicular to the longitudinal extension, wherein the longitudinal extension preferably exceeds the lateral extension by at least a factor 5, preferably by at least a factor 10. The sensor unit preferably may have a length of 5 mm-50 mm, preferably a length of 15 mm-40 mm and most preferably a length of 30 mm. The sensor unit may further have a width of 0.2 mm to 10 mm, preferably a width of 0.5 mm-5 mm, most preferably a width of 1 mm-3 mm at the connector part and a reduced width of 0.1 mm-2 mm, preferably a width of 0.4 mm-1 mm. However, other dimensions are possible.

Further preferred embodiments refer to the step of providing the electrically conductive material, preferably the electrically conductive organic material. Thus, as outlined above, the step of providing the sensor unit may imply fully or partially manufacturing the sensor unit. Thus, in step b), the at least one conductive path may fully or partially be manufactured by applying this at least one path to the connector substrate. For this purpose, one or more patterned films may be applied to the connector substrate, thereby generating the at least one conductive path or at least one part thereof.

For this purpose, preferably, the at least one electrically conductive material, preferably the electrically conductive organic material, may be applied to the connector substrate by an arbitrary method, such as by vapor deposition and/or by applying the electrically conductive material to the connector substrate from a liquid phase. This liquid phase may comprise at least one solution and/or at least one dispersion of the electrically conductive material. The application from a liquid phase is specifically preferred in case an electrically conductive organic material is used or, more preferably, an electrically conductive polymer. For applying the electrically conductive material from a liquid phase, several techniques may be used. Thus, spin-coating, doctor blading and/or printing techniques may be used. For patterning the at least one conductive path, several techniques may be applied, as will be outlined in further detail below. Thus, a large area application of the electrically conductive material may be used, followed by one or more patterning steps. Additionally or alternatively, a patterned application may be used, such as by applying the electrically conductive material in a patterned fashion, such as by using printing techniques or other pattern forming application techniques, thereby generating the patterns of the conductive path.

Additionally or alternatively to an application of the electrically conductive material, preferably the electrically conductive organic material, one or more other application or deposition techniques may be used. Thus, a deposition from the gas phase may be used, such as physical vapor deposition (PVD) and/or chemical vapor deposition (CVD). As an example, one or more metal materials may be deposited by sputtering or evaporation techniques. Similarly, conductive carbon materials such as graphite and/or glassy carbon and/or carbon nanotubes may be deposited by using vapor deposition techniques, such as growth from the vapor phase and/or evaporation.

Further, the electrically conductive material, preferably the electrically conductive organic material, may be applied to the connector substrate in a final chemical form and/or in a precursor form. Thus, the application of the at least one electrically conductive material may comprise an application of the electrically conductive material itself and/or of at least one precursor form which, after application, is transformed into the electrically conductive material, such as by polymerization and/or any other physical and/or chemical transformation.

As outlined above, the electrically conductive material, preferably the electrically conductive organic material, specifically may comprise at least one electrically conductive polymer. Various types of electrically conductive polymers are known in the art. Thus, the electrically conductive polymer may comprise an arbitrary polymer material having electric conductivity as defined above. Most preferably, polymers comprise an elongated π-electron system by providing a plurality of conjugated double bonds. Further, one or more dopants may be provided, such as by introducing electrical charges, such as for generating and/or increasing electrical conductivity. Preferably, the electrically conductive polymer is capable of being electrochemically oxidized and/or electrochemically reduced, thereby forming stable oxidized and/or reduced forms.

Various types of electrically conductive polymers are commercially available, such as by Heraeus Clevios GmbH, Germany, such as under the trade name "Clevios" (PEDOT: PSS). Most preferably, the electrically conductive organic material comprises at least one material selected from the group consisting of: poly-3,4-ethylendioxythiophene, preferably PEDOT:PSS; polyaniline; polypyrrole. However, additionally or alternatively, other types of electrically conductive materials, preferably electrically conductive organic materials, may be used, as the skilled person will recognize. Most preferably, the electrically conductive material, preferably the electrically conductive organic material, has an electric conductivity of at least 0.1 S/cm, preferably of at least 1.0 S/cm and most preferably of at least 10 S/cm or even of at least 100 S/cm.

Further preferred embodiments may refer to the sensor unit. As outlined above, the sensor unit preferably may be capable of performing electrochemical measurements of an analyte concentration in a body fluid of the user. Thus, preferably, the sensor unit may comprise at least two sensor electrodes, wherein the at least two sensor electrodes preferably are adapted for electrochemically determining at least one concentration of an analyte in a body tissue or a body fluid of the user. Thus, the at least two sensor electrodes preferably may comprise at least one working electrode adapted for measuring an electrode potential and/or a charge and/or a current which is influenced by the analyte concentration in the body tissue or the body fluid. Additionally, the at least two sensor electrodes may provide at least one counter electrode for current balancing and/or charge balancing. In addition, the at least two electrodes optionally may comprise at least one reference electrode. For further details or potential electrode setups, reference may be made to WO 2007/071562 A1. In this document, further, measurement setups and measurement methods are disclosed for using the electrode setup for electrochemical determination of an analyte concentration.

As outlined above, the at least two sensor electrodes preferably may comprise at least one working electrode. The working electrode preferably may have at least one detector substance adapted for performing at least one electrochemical reaction in the presence of the analyte. For potential embodiments of the detector substance, reference may be made to the documents disclosed above, such as to U.S. Pat. No. 5,413,690, U.S. Pat. No. 5,762,770, U.S. Pat. No. 5,798,031, U.S. Pat. No. 5,997,817, US 2009/0020502, WO 2009/056299, U.S. Pat. No. 6,360,888, US 2008/0242962 A1, WO 2007/071562 A1 or other documents. Specifically, the at least one detector substance may comprise at least one enzyme adapted for performing an appropriate detection reaction with the at least one analyte to be detected, such as glucose. Most preferably, the enzyme may comprise glucose oxidase. Additionally or alternatively, one or more other enzymes may be used. Thus, other enzymes may comprise glucose dehydrogenase as FAD-GDH, PQQ-GDH or FAD-GDH, or lactate oxidase or lactate dehydrogenase. Additionally or alternatively to the at least one enzyme, other materials may be comprised, such as at least one mediator and/or catalyst adapted for transferring electric charges, such as $MnO_2$. Other embodiments are feasible. The at least one detector substance preferably may be applied to at least one pad, such as at least one electrode pad of the working electrode. The at least one pad preferably may be comprised of a conductive material such as at least one metal. However, most preferably, the detector substance is applied to at least one pad of the electrically conductive material, preferably the electrically conductive organic material. Thus, the pad of the electrically conductive material may preferably form an end portion of the conductive path applied to the connector substrate. Thus, the pad of the electrically conductive material, preferably the electrically conductive organic material, may be formed by a round or rectangular or rounded pad applied to a substrate of the sensor unit, such as a common substrate which also provides the connector substrate, most preferably a flexible substrate of the connector unit.

As outlined above, further embodiments of the present invention may refer to the patterning of the conductive path. Thus, as outlined above, the conductive path may be applied to the connector substrate in a patterned fashion. Additionally or alternatively, the conductive path may be generated by applying the conductive organic material in an unpatterned fashion, followed by at least one patterning step. Thus, the step of providing the sensor unit may comprise one or more substeps of patterning the conductive path. Thus, the substep of patterning the conductive path may comprise at least one step of a large-area application of the electrically conductive material, preferably the electrically conductive organic material, to the connector substrate. As outlined above, preferably, this step of large-area application may comprise an application from a liquid phase, such as by spin-coating, doctor-blading or any other large-area application. The step of large-area application may be followed by at least one step of patterned removal of the electrically conductive material, preferably the electrically conductive organic material, in some regions of the connector substrate. Thus, the electrically conductive material may be removed in regions outside the conductive path. The removal of the electrically conductive material may be performed by any arbitrary removal method, such as by wet-chemical methods and/or by etching methods and/or by ablation methods, such as by laser ablation. Thus, as an example, for the purpose of laser ablation, a $CO_2$ laser may be used, such as a pulsed $CO_2$ laser. However, other techniques are feasible.

As further outlined above, the conductive path may be applied in a patterned fashion. Thus, the substep of patterning the electrically conductive material, preferably the electrically conductive organic material, may fully or partially be combined with a step of applying the electrically conductive material to the connector substrate. Thus, the substep of patterning the conductive path may comprise at least one printing step, wherein the electrically conductive material, preferably the electrically conductive organic material, is printed onto the connector substrate in a patterned fashion. Therein, various types of printing techniques may be used. Thus, the printing step preferably may use one or more of the following printing techniques: inkjet printing, screen printing, stencil printing, tampon printing, flexo-printing, laser transfer printing. An example of a laser transfer printing method is disclosed in DE 10 2007 026 883 A1. However, in addition or alternatively, other types of printing techniques may be used.

The at least one conductive path, as outlined above, comprises the at least one electrically conductive material. Preferably, the electrically conductive material comprises at least one electrically conductive organic material and, more preferably, at least one electrically conductive polymer. Additionally or alternatively, the conductive path and, more specifically, the electrically conductive material may comprise other types of electrically conductive materials, such as metals, e.g. copper, nickel, preferably noble metals like silver, gold, palladium or platinum, in pure, layered, or alloy form. However, most preferably, the conductive path solely consists of an electrically conductive organic material and, more preferably, solely consists of an electrically conductive polymer.

The conductive path may consist of precisely one electrically conductive material. Alternatively, the conductive path may comprise more than one electrically conductive material. Thus, as an example, the conductive path may comprise a noble metal, such as at least one metal layer comprising a noble metal such as gold and/or platinum, and at least one other electrically conductive material, such as at least one additional layer made of a non-metallic conductive material such as an electrically conductive organic material and/or of an additional metallic material.

The conductive path preferably may have a layer thickness of 0.01 μm-10 μm. Thus, layer thicknesses of 0.1 μm-8 μm may be used. The conductive path preferably may have an electrical resistance of at most 50 kΩ. This electrical resistance may be measured from a sensor electrode to a corresponding electric contact pad, wherein the sensor electrode and the electric contact pad are interconnected by the conductive path.

The sensor unit may comprise a common or uniform substrate. The connector substrate itself may form part of this uniform substrate of the sensor unit. Thus, as an example, the sensor unit may comprise a sensor unit substrate, wherein the connector substrate is a part of the sensor unit substrate. Preferably, the sensor unit substrate is a flexible substrate, such as a flexible plastic substrate. As an example, the sensor unit substrate and/or the connector substrate may comprise at least one plastic substrate, more preferably at least one plastic substrate comprising at least one polyester material. As an example, PET (polyethylene terephthalate) may be used. Most preferably, the connector substrate and/or the sensor unit substrate may have a thickness of 100 μm-1 mm, preferably of 200 μm-500 μm and, more preferably, of 300 μm-400 μm. However, other embodiments are feasible.

Further preferred embodiments may refer to the step of providing the sensor unit. Thus, as an example, step b) may comprise providing a plurality of sensor units on a common substrate. Thus, a batch production of sensor units on a large-area substrate may be performed. The method may further comprise at least one cutting step, wherein the sensor units are cut from the common substrate, preferably by at least one of a die cutting process and a laser cutting process.

As outlined above, the sensor unit preferably may comprise a plurality of conductive paths. Each conductive path may have at least one connector portion. Thus, as outlined above, a plurality of sensor electrodes may be provided, wherein a corresponding number of connector portions is provided, wherein the conductive paths are adapted to electrically connect the sensor electrode to a corresponding connector portion, thereby allowing for electrically contacting the corresponding sensor electrode via a corresponding connector portion.

Correspondingly, the evaluation unit may comprise a plurality of electric paths. As outlined above, in the alignment step, each connector portion may be aligned to a corresponding electric contact pad. Therein, a 1:1 alignment may be provided. However, as outlined above, other types of alignments may be provided, such as a 2:1 alignment and/or a 1:2 alignment. Thus, for each connector portion, one or more corresponding electric contact pads may be provided. Alternatively, for each electric contact pad, one or more corresponding connector portions may be provided.

As further outlined above, further optional embodiments of the invention may refer to the application of the anisotropic conductive adhesive. Thus, the anisotropic conductive adhesive may be provided commonly for a plurality of the connector portions and/or for a plurality of the electric contact pads, preferably in an un-patterned fashion, without the need of adapting the shape of the anisotropic conductive adhesive to the shape of the connector portions and/or of the electric contact pads. Thus, in the preparation step, an amount of the anisotropic conductive adhesive may commonly be applied for the plurality of the connector portions and the plurality of the electric contact pads. Therein, in the bonding step, the anisotropic conductive adhesive may provide the electric connection between corresponding connector portions and corresponding electric contact pads. Contrarily, due to the anisotropy of the anisotropic conductive adhesive, non-corresponding electric contact pads and connector portions as well as neighboring pairs of connector portions and neighboring pairs of electric contact pads may be electrically insulated against each other, preferably with a resistance of at least $10^8 \Omega$ or at least $10^9 \Omega$.

As outlined above, in the preparation step, the anisotropic conductive adhesive may be applied in an amorphous form and/or as a film, preferably as a liquid and/or as a paste. The anisotropic conductive adhesive may be applied by at least one dispending process and/or at least one printing process. Other types of application processes are possible. The application generally may take place to the evaluation unit substrate in the region of the at least one electric contact pad and/or to the connector substrate in the region of the at least one connector portion. Therein, preferably, a plurality of the connector portions and/or a plurality of the electric contact pads may be covered simultaneously by the same amount of anisotropic conductive adhesive.

Further, in the preparation step, the anisotropic conductive adhesive may be applied excessively such that, after performing the bonding step, a bead of excess anisotropic conductive adhesive may be formed at at least one edge of the evaluation unit substrate and/or the connector substrate. Thus, the at least one evaluation unit substrate and the at least one connector substrate may overlap in the region of the electric contact pad and the connector portion, thereby forming an overlap region, which, later on, will be provide the electric connection between the sensor unit and the evaluation unit. At the edges of the overlap, one or more beads of excess anisotropic conductive adhesive may be formed, thereby providing an additional mechanical stability in the overlap region. Thus, generally, in this embodiment or other embodiments, the anisotropic conductive adhesive may provide both an electric interconnection and a mechanical interconnection in between the evaluation unit and the sensor unit. Thus, preferably, besides the interconnection provided by the anisotropic conductive adhesive, no further connection element is required, such as clamps and/or any other type of mechanical interconnection. However, other types of connection elements may be provided in addition.

The at least one anisotropic conductive adhesive, as outlined above, preferably may be provided in an amorphous form and/or as a film, preferably in a deformable form, such as in a liquid form and/or a paste. Additionally or alternatively, the at least one anisotropic conductive adhesive may comprise at least one anisotropic conductive adhesive film.

As outlined above, the at least one anisotropic conductive adhesive may comprise electrically conductive particles. The electrically conductive particles preferably may have an average particle size defined by an equivalent diameter.

In the bonding step, the anisotropic conductive adhesive preferably may be compressed to a layer thickness of less than 20 µm and, most preferably, to a layer thickness of less than 10 µm or even less than 5 µm. The optimum layer thickness may depend on the particle size of the electrically conductive particles which optionally may be contained in the anisotropic conductive adhesive. Thus, preferably, the layer thickness of the anisotropic conductive adhesive is chosen by appropriate compression. Thus, as an example, the layer thickness may be equal to the average particle size, may be in the range of the average particle size or may even be below the average particle size of the electrically conductive particles, thereby allowing for the electrically conductive particles to create an electrical connection between one surface of the layer of the anisotropic conductive adhesive to an opposing surface, whereas, in a plane perpendicular to this direction, the particles are separated by the optional matrix material, thereby providing electrical insulation in this plane. As an example, in the bonding step, the anisotropic conductive adhesive may be compressed to a layer thickness of less than 100% of the diameter of the respective conductive particles, preferably to less than 80%.

As outlined above, in the bonding step, preferably, one or more of pressure, heat and radiation may be applied, such as to the connector substrate and/or the evaluation unit substrate, preferably in the region of the connector portion and/or in the region of the electric contact pad. The radiation may be selected from the group consisting of electromagnetic radiation, such as electromagnetic radiation in the ultraviolet spectral range, the visible spectral range or the infrared spectral range, and particular radiation, such as an electron radiation. As an example, pressure and heat may be applied, or pressure and radiation may be applied. Thus, preferably, heat may be applied to be part of the evaluation unit substrate containing the electric contact pad and/or to a part of the connector substrate containing the connector portion, such as from an opposing site, i.e. a side of the evaluation unit substrate opposing the electric contact pad and/or from a side of the connector substrate opposing the connector portion. Thus, as outlined above, heat may be applied by using at least one heated stamp. Generally, a temperature of 80° C. to 220° C. may be applied, preferably a temperature of 100° C. to 200° C. and, more preferably, a temperature of 150° C. to 180° C. However, other embodiments are feasible.

Further, as outlined above, in the bonding step, a pressure of 10 N-100 N may be applied, preferably a pressure of 20 N-60 N. In terms of pressures given in MPa, reference may be made to the above-mentioned preferred pressures.

As outlined above, an overlap may be created in the preparation step between the evaluation unit substrate and the connector substrate. Thus, the preparation step may be performed such that the evaluation unit substrate and the connector substrate overlap in an overlap area. The overlap area preferably has a dimension of 1 mm²-50 mm², preferably 25 mm²-20 mm² and, most preferably, 15 mm². However, other dimensions are feasible.

Further preferred embodiments of the method may refer to a sterilization of the device, the evaluation unit, the sensor unit or parts thereof. Thus, most preferably, after performing the bonding step, the device may at least partially be sterilized. For sterilization, preferably, a radiation sterilization may be used, more preferably a sterilization by an electron radiation, such as a β-sterilization. As an example, electron beams providing a dose of 5 kGy-50 kGy may be used, more preferably 10 kGy-40 kGy and, most preferably, 20 kGy-30 kGy and, specifically, 25 kGy.

In a further aspect of the present invention, a device for monitoring at least one body function of a user is disclosed. As outlined in further detail below, the device preferably may be obtainable by using the method according to one or more of the above-mentioned methods and/or by using one or more of the embodiments of the method disclosed in further detail below. Additionally or alternatively, the method may be adapted for generating a device according to the present invention. Thus, for further optional details of the device, reference may be made to the method according to the invention, and, vice versa, for further optional details of the method, reference may be made to the disclosure of the device according to the present invention. However, other embodiments are feasible.

The device comprises at least one evaluation unit and at least one sensor unit. The evaluation unit has at least one electric contact pad applied to at least one evaluation unit substrate. The electric contact pad is electrically connected to at least one electronic device of the evaluation unit. The sensor unit comprises at least one connector part, wherein the connector part comprises at least one connector substrate and at least one conductive path applied to the connect- or substrate. The connector path comprises at least one electrically conductive material, preferably at least one electrically conductive organic material and, more preferably, at least one electrically conductive polymer. Additionally or alternatively, one or more other types of electrically conductive materials may be used, such as one or more of the electrically conductive materials listed above. The conductive path has at least one connector portion. The connector portion is aligned next to the electric contact pad such that the connector portion faces the electric contact pad. At least one anisotropic conductive adhesive is provided in between the electric contact pad and the connector portion. The evaluation unit substrate and the connector substrate are connected such that an electric connection of the electric contact pad and the connector portion is created via the anisotropic conductive adhesive. Therein, preferably, the anisotropic conductive adhesive may be present in a hardened form, such as after a curing or setting process. Thus, in step d) of the method disclosed above, i.e. the bonding step, one or more of pressure, heat and radiation may be applied in order to create the electric connection of the electric contact pad and the connector portion. By applying the pressure and/or the heat and/or the radiation, the anisotropic conductive adhesive may be compressed to a thin layer, such as a thin layer having the thickness as disclosed above, thereby creating an electric connection in between the electric contact pad and the connector portion. Further, a curing process may be initiated, thereby hardening the anisotropic conductive adhesive, such that, when the heat and/or the pressure and/or the radiation are removed, the anisotropic conductive adhesive remains in the form of a thin film, electrically connecting the electric contact pad and the connector portion, whereas, due to the anisotropic conductive properties, in an arbitrary direction perpendicular to the interconnection, insulating properties are provided.

The method and the device according to the present invention provide a large number of advantages over known methods and devices. Thus, astonishingly, it was found in a series of experiments that reliable interconnections between the evaluation unit and the sensor unit, providing both electrical connections and mechanical connections, may be generated in a simple fashion by using the anisotropic conductive adhesive. Thus, a simple contacting process may be realized. For performing the method, a small amount of the anisotropic conductive adhesive, such as an amount of less than 10 µl, preferably of less than 2 µl may be applied to the at least one electric contact pad and/or to the at least one connector portion. Further, the alignment may take place, such as by aligning the part of the connector substrate containing the connector portion on the part of the evaluation unit substrate containing the electric contact pad and by applying pressure. Therein, a thin, continuous adhesive film may be generated over one, more than one or even all of the electric contact pads and/or one, more than one or even all of the connector portions. The pressure may easily be applied by using a heatable stamp.

The pressure creates an electric contact between the connector portion and the electric contact pad, via the anisotropic conductive adhesive, such as via the particles contained therein, such as gold particles and/or particles coated with a metal such as gold. By applying heat, a curing process may easily be induced, such as a thermosetting process. Thereby, by using a curing process, a permanent mechanically robust electrically conducting interconnection may be created. Surprisingly, in the experiments disclosed in further detail below, it was found out that, even when a fine patterning is used, an electric resistance of the anisotropic conductive adhesive in between the electrodes may exceed $10^9 \Omega$. The gluing connection by using the anisotropic conductive adhesive turned out to be mechanically robust, preferably when using additional beads of excess anisotropic conductive adhesive, preferably at edges of the evaluation unit substrate and/or the connector substrate in an overlap region. An adhesion of the electrically conductive adhesive to one or more of the connector substrate, the evaluation unit substrate, the connector portion and the electric contact pad may further be increased by an optional step of plasma cleaning or plasma etching of one or more of these elements before applying the electrically conductive adhesive. Thus, it was found that the adhesion of the anisotropic conductive adhesive to a contact pad fully or partially made of a metal, such as gold, was significantly increased when the contact pad had previously been subject to a cleaning step using an atmospheric plasma cleaning process.

Further, surprisingly, it turned out that the bonding using the anisotropic conductive adhesive was highly resistant to sterilization processes. Thus, both the mechanical interconnection and the electric interconnection through the anisotropic conductive adhesive turned out to be robust against an electron beam sterilization having a dose of 25 kGy, without deterioration of the electrical contact or without increasing an unwanted conductivity between neighboring electrodes.

Further, the method according to the present invention may easily be realized in a large-scale manufacturing process having a high throughput. Thus, preferably, a reel-to-reel process may be implemented, thereby creating a large number of sensor units on a common substrate. Subsequently, the sensor units may be singularized and bonded to the evaluation unit, by using the method according to the present invention and by using the anisotropic conductive adhesive. Thus, a cost-effective large-scale process having a high throughput may be realized.

Summarizing the findings of the present invention, the following embodiments are preferred:

Embodiment 1

A method for manufacturing a device for monitoring at least one body function of a user, wherein the device comprises at least one evaluation unit and at least one sensor unit, wherein the method comprises the following steps:

a) a step of providing the evaluation unit, wherein the evaluation unit has at least one electric contact pad applied to at least one evaluation unit substrate, wherein the electric contact pad is electrically connected to at least one electronic device of the evaluation unit;
b) a step of providing the sensor unit, wherein the sensor unit comprises at least one connector part, wherein the connector part comprises at least one connector substrate and at least one conductive path applied to the connector substrate, wherein the conductive path comprises at least one electrically conductive material, preferably at least one electrically conductive organic material and, more preferably, at least one electrically conductive polymer, and wherein the conductive path has at least one connector portion, preferably at least one pad-shaped connector portion;
c) a preparation step, wherein the connector portion is aligned next to the electric contact pad such that the connector portion faces the electric contact pad, wherein at least one anisotropic conductive adhesive is provided in between the electric contact pad and the connector portion;
d) a bonding step, wherein the evaluation unit substrate and the connector substrate are pressed together, wherein the electric contact pad and the connector portion are pressed together, wherein an electric connection of the electric contact pad and the connector portion is created via the anisotropic conductive adhesive.

Embodiment 2

The method according to the preceding embodiment, wherein the sensor unit comprises at least one implantable sensor unit, wherein the implantable sensor unit comprises at least one implantable portion adapted for implantation into a body tissue of the user.

Embodiment 3

The method according to one of the preceding embodiments, wherein the sensor unit has an elongated shape having a longitudinal extension and a lateral extension, wherein the longitudinal extension exceeds the lateral extension by at least a factor 5, preferably by at least a factor 10.

Embodiment 4

The method according to one of the preceding embodiments, wherein the sensor unit has a length of 5 mm to 50 mm, preferably a length of 15 mm to 40 mm and most preferably a length of 30 mm.

Embodiment 5

The method according to one of the preceding embodiments, wherein the sensor unit has a width of 0.2 mm to 10 mm, preferably a width of 0.5 mm to 5 mm and most preferably a width of 1 mm to 3 mm.

Embodiment 6

The method according to one of the preceding embodiments, wherein the step of providing the sensor unit comprises a step of applying the electrically conductive material, preferably the electrically conductive organic material, to the connector substrate from a liquid phase.

Embodiment 7

The method according to the preceding embodiment, wherein the liquid phase comprises at least one of a solution and a dispersion of the electrically conductive material, preferably the electrically conductive organic material.

Embodiment 8

The method according to one of the preceding embodiments, wherein the electrically conductive material comprises at least one electrically conductive organic material, preferably at least one electrically conductive polymer.

Embodiment 9

The method according to one of the preceding embodiments, wherein the electrically conductive material comprises at least one material selected from the group consisting of:
an electrically conductive organic material, preferably at least one electrically conductive polymer and, more preferably, at least one electrically conductive polymer selected from the group consisting of poly-3,4-ethylendioxythiophene, preferably PEDOT:PSS, polyaniline and polypyrrole;
an electrically conductive carbon material, preferably one or more of graphite, glassy carbon, graphene and carbon nanotubes;
a metal, preferably a metal selected from the group consisting of Cu, Ni, Ag, Au, Pd and Pt.

Embodiment 10

The method according to one of the preceding embodiments, wherein the electrically conductive material, preferably the electrically conductive organic material, has an electric conductivity of at least 0.1 S/cm, preferably of at least 1.0 S/cm and most preferably of at least 100 S/cm.

Embodiment 11

The method according to one of the preceding embodiments, wherein the sensor unit comprises at least two sensor electrodes, wherein the at least two sensor electrodes are adapted for electrochemically determining at least one concentration of an analyte in a body tissue or body fluid of the user.

Embodiment 12

The method according to the preceding embodiment, wherein the sensor electrodes comprise at least one working electrode, the working electrode having at least one detector substance adapted for performing at least one electrochemical reaction in the presence of the analyte.

Embodiment 13

The method according to the preceding embodiment, wherein the detector substance comprises at least one enzyme, preferably one of glucose oxidase, glucose dehydrogenase (FAD-GDH or PQQ-GDH or NAD-GDH), lactate oxidase, lactate dehydrogenase.

Embodiment 14

The method according to one of the preceding embodiments, wherein the detector substance is applied to at least one pad of the electrically conductive material, preferably the electrically conductive organic material.

Embodiment 15

The method according to one of the preceding embodiments, wherein the step of providing the sensor unit comprises at least one substep of patterning the conductive path.

Embodiment 16

The method according to the preceding embodiment, wherein the substep of patterning the conductive path comprises a step of large-area application of the electrically conductive material, preferably the electrically conductive organic material, to the connector substrate and a step of structured removal of the electrically conductive material, preferably the electrically conductive organic material, in some regions of the connector substrate, preferably by laser ablation.

Embodiment 17

The method according to one of the two preceding embodiments, wherein the substep of patterning the conductive path comprises at least one printing step, wherein the electrically conductive material, preferably the electrically conductive organic material, is printed onto the connector substrate in a patterned fashion.

Embodiment 18

The method according to the preceding embodiment, wherein the printing step uses a printing technique selected from the group consisting of: inkjet printing, screen printing, stencil printing, tampon printing, flexo printing, laser transfer printing.

Embodiment 19

The method according to one of the preceding embodiments, wherein the conductive path solely consists of the electrically conductive material, preferably the electrically conductive organic material.

Embodiment 20

The method according to one of the preceding embodiments, wherein the conductive path comprises more than one electrically conductive material, preferably of a noble metal and at least one other electrically conductive material.

Embodiment 21

The method according to one of the preceding embodiments, wherein the conductive path has a layer thickness of 0.01 µm to 10 µm.

Embodiment 22

The method according to one of the preceding embodiments, wherein the conductive path, preferably from a sensor electrode to an electric contact pad, has an electrical resistance of at most 50 kΩ.

Embodiment 23

The method according to one of the preceding embodiments, wherein the connector substrate is part of a uniform substrate of the sensor unit.

Embodiment 24

The method according to one of the preceding embodiments, wherein the connector substrate comprises at least one plastic substrate.

Embodiment 25

The method according to the preceding claim, wherein the plastic substrate comprises at least one polyester.

Embodiment 26

The method according to one of the preceding embodiments, wherein the connector substrate has a layer thickness of 100 µm to 1 mm, preferably of 200 µm to 500 µm and more preferably of 300 µm to 400 µm.

Embodiment 27

The method according to one of the preceding embodiments, wherein step b) comprises providing a plurality of sensor units on a common substrate and, further, at least one cutting step, wherein the sensor units are cut from the common substrate, preferably by at least one of a die cutting process and a laser cutting process.

Embodiment 28

The method according to one of the preceding embodiments, wherein the connector substrate is flexible or deformable.

Embodiment 29

The method according to one of the preceding embodiments, wherein the sensor unit comprises a plurality of conductive paths, each conductive path having at least one connector portion, wherein the evaluation unit comprises a plurality of electric contact pads, wherein, in the alignment step, each connector portion is aligned to a corresponding electric contact pad.

Embodiment 30

The method according to the preceding embodiment, wherein, in the preparation step, an amount of the anisotropic conductive adhesive is commonly applied to the plurality of the connector portions and the plurality of the electric contact pads, wherein, in the bonding step, the anisotropic conductive adhesive provides the electric connection between corresponding connector portions and electric contact pads, whereas, due to the anisotropy of the anisotropic conductive adhesive, non-corresponding electric contact pads and connector portions as well as neighboring pairs of connector portions and neighboring pairs of electric contact pads are electrically insulated against each other, preferably with a resistance of at least $10^8 \Omega$ or at least $10^9 \Omega$.

Embodiment 31

The method according to one of the preceding embodiments, wherein, in the preparation step, the anisotropic conductive adhesive is applied as a film and/or in an amorphous form, preferably as a liquid and/or as a paste.

Embodiment 32

The method according to one of the preceding embodiments, wherein, in the preparation step, the anisotropic conductive adhesive is applied by at least one of a dispensing process and a printing process.

Embodiment 33

The method according to one of the preceding embodiments, wherein, in the preparation step, the anisotropic conductive adhesive is applied excessively such that, after performing the bonding step, a bead of excess anisotropic conductive adhesive is formed at at least one edge of at least one of the evaluation unit substrate and the connector substrate.

Embodiment 34

The method according to one of the preceding embodiments, wherein the at least one anisotropic conductive adhesive comprises an anisotropic conductive adhesive film.

Embodiment 35

The method according to one of the preceding embodiments, wherein the anisotropic conductive adhesive comprises electrically conductive particles.

Embodiment 36

The method according to the preceding embodiment, wherein the electrically conductive particles have an average particle size of 0.5 µm to 10 µm, preferably of 1 µm to 5 µm and more preferably of 3 µm.

Embodiment 37

The method according to one of the preceding embodiments, wherein, in the bonding step, the anisotropic conductive adhesive is compressed to a layer thickness of less than 100% of the diameter of the respective conductive particles, preferably to less than 80%.

Embodiment 38

The method according to one of the preceding claims, wherein, in the bonding step, one or more of pressure, heat and radiation are applied, preferably to the evaluation unit substrate and/or to the connector substrate, and more preferably to a part of the evaluation unit substrate containing the electric contact pad and/or to a part of the connector substrate containing the connector portion, such as by applying pressure and heat and/or by applying pressure and radiation.

Embodiment 39

The method according to the preceding embodiment, wherein, in the bonding step, one or more of pressure, heat and radiation are applied to at least one of the evaluation unit substrate and the connector substrate in the region of the electric contact pad and the connector portion, such as by applying pressure and heat and/or by applying pressure and radiation.

Embodiment 40

The method according to one of the two preceding embodiments, wherein a temperature of 80° C. to 220° C. is applied, preferably a temperature of 100° C. to 200° C. and more preferably a temperature of 150° C. to 180° C.

Embodiment 41

The method according to one of the three preceding embodiments, wherein a heated stamp is used for applying heat.

Embodiment 42

The method according to one of the preceding embodiments, wherein, in the bonding step, a pressure of 10 N to 100 N is applied, preferably a pressure of 20 N to 60 N.

Embodiment 43

The method according to one of the preceding embodiments, wherein the preparation step is performed such that the evaluation unit substrate and the connector substrate overlap in an overlap area of 1 mm$^2$ to 50 mm$^2$, preferably in an overlap area of 5 mm$^2$ to 20 mm$^2$ and most preferably in an overlap area of 15 mm$^2$.

Embodiment 44

The method according to one of the preceding embodiments, wherein, after performing the bonding step, the device is at least partially sterilized by radiation sterilization, preferably by an electron radiation.

Embodiment 45

A device for monitoring at least one body function of a user, wherein the device comprises at least one evaluation unit and at least one sensor unit,
- wherein the evaluation unit has at least one electric contact pad applied to at least one evaluation unit substrate, wherein the electric contact pad is electrically connected to at least one electronic device of the evaluation unit,
- wherein the sensor unit comprises at least one connector part, wherein the connector part comprises at least one connector substrate and at least one conductive path applied to the connector substrate, wherein the conductive path comprises at least one electrically conductive material, preferably at least one electrically conductive organic material, and wherein the conductive path has at least one connector portion,
- wherein the connector portion is aligned next to the electric contact pad such that the connector portion faces the electric contact pad, wherein at least one anisotropic conductive adhesive is provided in between the electric contact pad and the connector portion,
- wherein the evaluation unit substrate and the connector substrate are connected such that an electric connection of the electric contact pad and the connector portion is created via the anisotropic conductive adhesive.

Embodiment 46

The device according to the preceding embodiment, wherein the device is obtainable by the method according to one of the preceding embodiments referring to a method.

Embodiment 47

The device according to one of the two preceding embodiments, wherein the sensor unit comprises at least one implantable sensor unit, wherein the implantable sensor unit comprises at least one implantable portion adapted for implantation into a body tissue of the user.

Embodiment 48

The device according to one of the preceding embodiments referring to a device, wherein the sensor unit has an elongated shape having a longitudinal extension and a lateral extension, wherein the longitudinal extension exceeds the lateral extension by at least a factor 5, preferably by at least a factor 10.

Embodiment 49

The device according to one of the preceding embodiments referring to a device, wherein the sensor unit has a length of 5 mm to 50 mm, preferably a length of 15 mm to 40 mm and most preferably and length of 30 mm.

Embodiment 50

The device according to one of the preceding embodiments referring to a device, wherein the sensor unit has a width of 0.2 mm to 10 mm, preferably a width of 0.5 mm to 5 mm and most preferably a width of 1 mm to 3 mm.

Embodiment 51

The device according to one of the preceding embodiments referring to a device, wherein the electrically conductive material, preferably the electrically conductive organic material, is applicable to the connector substrate from a liquid phase.

Embodiment 52

The device according to the preceding embodiment, wherein the liquid phase comprises at least one of a solution and a dispersion of the electrically conductive material, preferably the electrically conductive organic material.

Embodiment 53

The device according to one of the preceding embodiments referring to a device, wherein the electrically conductive material comprises at least one electrically conductive organic material, preferably at least one electrically conductive polymer.

Embodiment 54

The device according to one of the preceding embodiments referring to a device, wherein the electrically conductive material comprises at least one material selected from the group consisting of:

- an electrically conductive organic material, preferably at least one electrically conductive polymer and, more preferably, at least one electrically conductive polymer selected from the group consisting of poly-3,4-ethylendioxythiophene, preferably PEDOT:PSS, polyaniline and polypyrrole;
- an electrically conductive carbon material, preferably one or more of graphite, graphene, glassy carbon and carbon nanotubes;
- a metal, preferably a metal selected from the group consisting of Cu, Ni, Ag, Au, Pd and Pt.

Embodiment 55

The device according to one of the preceding embodiments referring to a device, wherein the electrically conductive material, preferably the electrically conductive organic material, has an electric conductivity of at least 0.1 S/cm, preferably of at least 1.0 S/cm and most preferably of at least 100 S/cm.

Embodiment 56

The device according to one of the preceding embodiments referring to a device, wherein the sensor unit comprises at least two sensor electrodes, wherein the at least two sensor electrodes are adapted for electrochemically determining at least one concentration of an analyte in a body tissue or body fluid of the user.

Embodiment 57

The device according to one of the preceding embodiments referring to a device, wherein the sensor electrodes comprise at least one working electrode, the working electrode having at least one detector substance adapted for performing at least one electrochemical reaction in the presence of the analyte.

Embodiment 58

The device according to one of the preceding embodiments referring to a device, wherein the detector substance comprises at least one enzyme, preferably one of glucose oxidase, glucose dehydrogenase (FAD-GDH or PQQ-GDH or NAD-GDH), lactate oxidase, lactate dehydrogenase.

Embodiment 59

The device according to one of the preceding embodiments referring to a device, wherein the detector substance is applied to at least one pad of the electrically conductive material, preferably the electrically conductive organic material.

Embodiment 60

The device according to one of the preceding embodiments referring to a device, wherein the conductive path solely consists of the electrically conductive material, preferably the electrically conductive organic material.

Embodiment 61

The device according to one of the preceding embodiments referring to a device, wherein the conductive path comprises more than one electrically conductive material, preferably of a noble metal and at least one other electrically conductive material.

Embodiment 62

The device according to one of the preceding embodiments referring to a device, wherein the conductive path has a layer thickness of 0.01 µm to 10 µm.

Embodiment 63

The device according to one of the preceding embodiments referring to a device, wherein the conductive path, preferably from a sensor electrode to an electric contact pad, has an electrical resistance of at most 50 kΩ.

Embodiment 64

The device according to one of the preceding embodiments referring to a device, wherein the connector substrate is part of a uniform substrate of the sensor unit.

Embodiment 65

The device according to one of the preceding embodiments referring to a device, wherein the connector substrate comprises at least one plastic substrate.

Embodiment 66

The device according to the preceding embodiment, wherein the plastic substrate comprises at least one polyester.

Embodiment 67

The device according to one of the preceding embodiments referring to a device, wherein the connector substrate has a layer thickness of 100 µm to 1 mm, preferably of 200 µm to 500 µm and more preferably of 300 µm to 400 µm.

Embodiment 68

The device according to one of the preceding embodiments referring to a device, wherein the connector substrate is flexible or deformable.

Embodiment 69

The device according to one of the preceding embodiments referring to a device, wherein the sensor unit comprises a plurality of conductive paths, each conductive path having at least one connector portion, wherein the evaluation unit comprises a plurality of electric contact pads, wherein, in the alignment step, each connector portion is aligned to a corresponding electric contact pad.

Embodiment 70

The device according to one of the preceding embodiments referring to a device, wherein the anisotropic conductive adhesive is applied excessively such that a bead of excess anisotropic conductive adhesive is formed at at least one edge of at least one of the evaluation unit substrate and the connector substrate.

Embodiment 71

The device according to one of the preceding embodiments referring to a device, wherein the at least one anisotropic conductive adhesive comprises an anisotropic conductive adhesive film.

Embodiment 72

The device according to one of the preceding embodiments referring to a device, wherein the anisotropic conductive adhesive comprises electrically conductive particles.

Embodiment 73

The device according to the preceding embodiment, wherein the electrically conductive particles have an average particle size of 0.5 µm to 10 µm, preferably of 1 µm to 5 µm and more preferably of 3 µm.

Embodiment 74

The device according to one of the preceding embodiments referring to a device, wherein the anisotropic conductive adhesive is compressed to a layer thickness of less than 100% of the diameter of the respective conductive particles, preferably to less than 80%.

Embodiment 75

The device according to one of the preceding embodiments referring to a device, wherein the evaluation unit substrate and the connector substrate overlap in an overlap area of 1 mm$^2$ to 50 mm$^2$, preferably in an overlap area of 5 mm$^2$ to 20 mm$^2$ and most preferably in an overlap area of 15 mm$^2$.

BRIEF DESCRIPTION OF THE SEVERAL VIEWS OF THE DRAWINGS

The following detailed description of the embodiments of the present invention can be best understood when read in conjunction with the following drawings. Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

In the Figures.

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

In FIGS. 1-4, in several views, an exemplary embodiment of a device 110 for monitoring at least one body function of a user is depicted. In the following, reference is made to all of these figures.

Figure 1:
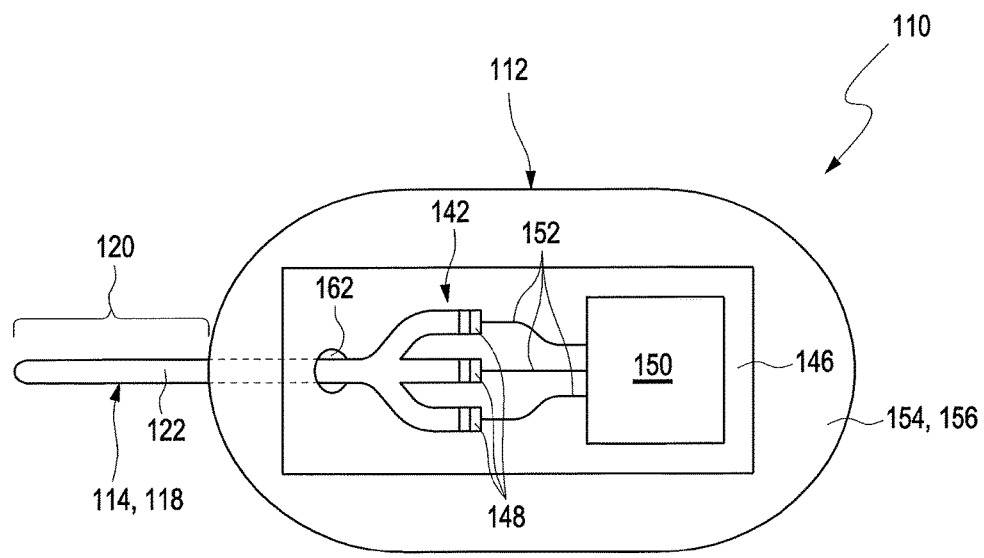
FIG. 1 shows a top view of an embodiment of a device for monitoring at least one body function of a user.
Figure 3:
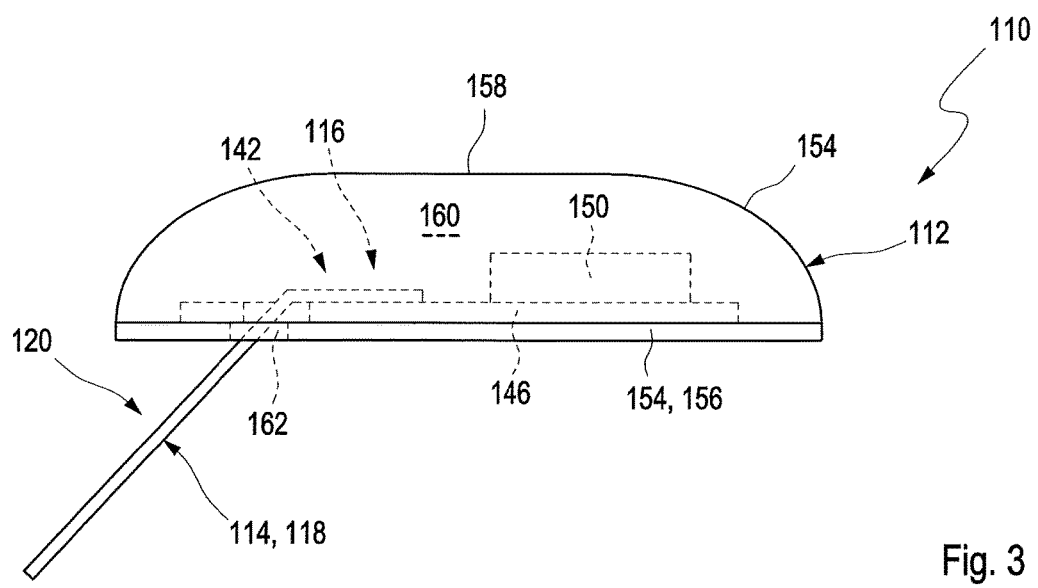
FIG. 3 shows a side view of the device according to FIG. 1.
Figure 4:
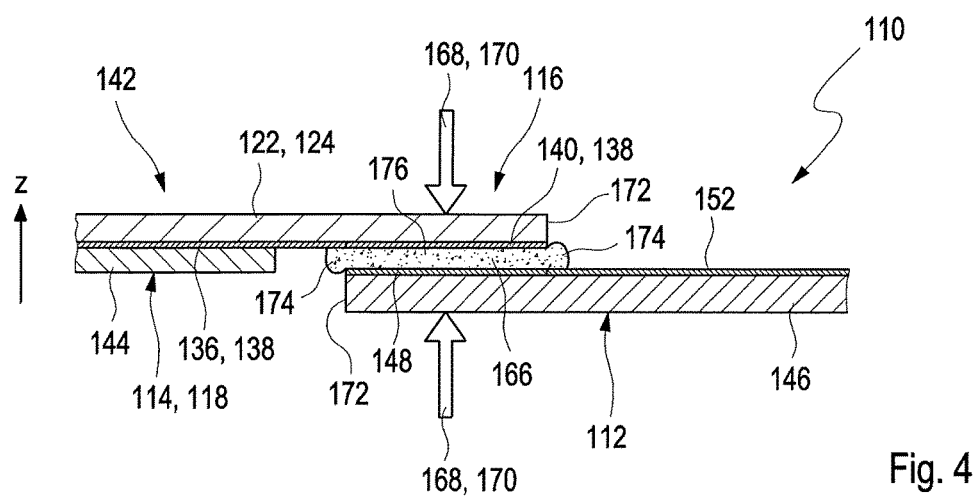
FIG. 4 shows a cross-sectional view of an overlap area of the device according to FIG. 1.

The device 110 comprises an evaluation unit 112 and a sensor unit 114. Therein, FIG. 1 shows a top view of the device 110, with the evaluation unit 112 in an opened state, FIG. 2 shows a top view of an exemplary embodiment of the sensor unit 114 which may be used in the device 110 according to FIG. 1, FIG. 3 shows a side view of the device 110, with the evaluation unit 112 in a closed state, and FIG. 4 shows a detailed view of a connection region 116 in which a mechanical and electrical connection in between the evaluation unit 112 and the sensor unit 114 is provided.

Figure 2:
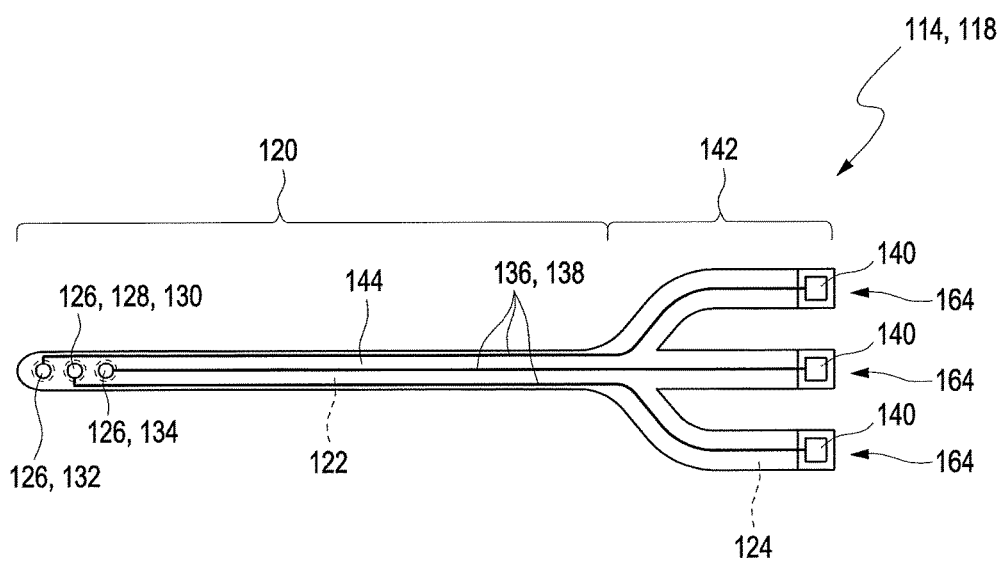
FIG. 2 shows a top view of a sensor unit which may be used in the device according to FIG. 1.

As depicted in FIG. 2, the sensor unit 114 specifically may comprise an implantable sensor unit 118 having at least one implantable portion 120 adapted for implantation into a body tissue of the user. The implantable portion 120 may protrude from the evaluation unit 112, thereby allowing for the evaluation unit 112 to rest on a body surface of the user, whereas the implantable portion 120 protrudes into the body tissue.

As specifically depicted in FIG. 2, the sensor unit 114 may comprise a sensor unit substrate 122, a part of which is formed by a connector substrate 124. As will be outlined in further detail below, the connector substrate 124 and the sensor unit substrate 122 preferably may be formed by using a flexible plastic material.

The sensor unit 114 further comprises at least two sensor electrodes 126. Therein, the sensor electrodes 126 preferably comprise at least one working electrode 128 having at least one detector substance 130 such as an enzyme, at least one counter electrode 132 and, optionally, at least one reference electrode 134. The sensor electrodes 126 are electrically connected to conductive paths 136, which are fully or partially formed by an electrically conductive material 138, preferably an electrically conductive organic material such as an electrically conductive polymer. The conductive paths 136 extend from respective sensor electrodes 126 to a plurality of connector portions 140 located in a connector part 142 of the sensor unit 114. In this embodiment, as an example, each sensor electrode 126 may be contacted via one respective connector portion 140. However, other embodiments are feasible.

Further, as indicated in FIG. 2, the sensor unit 114 may fully or partially be covered by at least one insulating layer 144. This insulating layer 144 may cover the conductive paths 136 such that the sensor electrodes 126 and the connector portions 140 remain uncovered, whereas remaining parts of the conductive paths 136 are covered, thereby providing an electrical insulation between the conductive paths 136 and the surrounding body tissue in an implanted state. Further, additionally or alternatively to the optional insulating layer 144, which, as an example, may comprise at least one insulating resin or photoresist, other types of coverage may be provided. Thus, as discussed in further detail above, the implantable sensor unit 118 may fully or partially be covered by at least one membrane, which is not depicted in the figures. Thus, the at least one membrane specifically may cover the working electrode 128 and/or other electrodes of the sensor electrodes 126. As an example, a semi-permeable membrane may be provided, which renders the sensor unit 114 biocompatible by preventing the detector substance 130 from migrating into the body tissue, simultaneously allowing for the analyte to be detected to migrate to the detector substance 130 and/or allowing for an electrolyte such as water to permeate the semi-permeable membrane to the sensor electrodes 126.

The evaluation unit 112, as depicted specifically in FIGS. 1 and 3, comprises at least one evaluation unit substrate 146 such as a printed circuit board. Thereon, a plurality of electric contact pads 148 is provided. The electric contact pads 148 are electrically connected to at least one electronic device 150 via a plurality of leads 152. Thus, the electronic device 150 may comprise one or more potentiostats.

The evaluation unit 112 may further comprise one or more casings 154, such as a casing having a bottom part 156 or patch which might be applicable to a body surface of the user, and/or a top part 158 or cover which fully or partially encloses an inner space 160 of the evaluation unit 112.

Not shown is an adhesive layer or adhesive patch to removably attach the evaluation unit to the skin of a user, which may be provided additionally.

As can be seen in FIGS. 1 and 3, the sensor unit 114 preferably is connected to the evaluation unit 112 with the connector part 142 fully or partially located inside the inner space 160. Via one or more openings 162 in the evaluation unit substrate 146 and/or the optional bottom part 156 of the casing 154, the sensor unit 114, specifically the implantable portion 120 of the sensor unit 114, may extend into a body tissue of the user, whereas the evaluation unit 112 may remain outside the body tissue. It has to be noted that other embodiments for connecting the sensor unit 114 to the evaluation unit 112 are feasible. Thus, instead of using one or more openings 162, one or more recesses or clearances may be provided, such as by the evaluation unit substrate 146 and/or by an optional bottom part 156 of the casing 154. Additionally or alternatively, the evaluation unit substrate may be inverted in order to have the contact pads 148 on the side facing the bottom part 156. Thereby, an extension of the implantable portion 120 of the sensor unit 114 into the evaluation unit 112, such as through openings 162 in the evaluation unit substrate 146, may be avoided.

Figure 5:
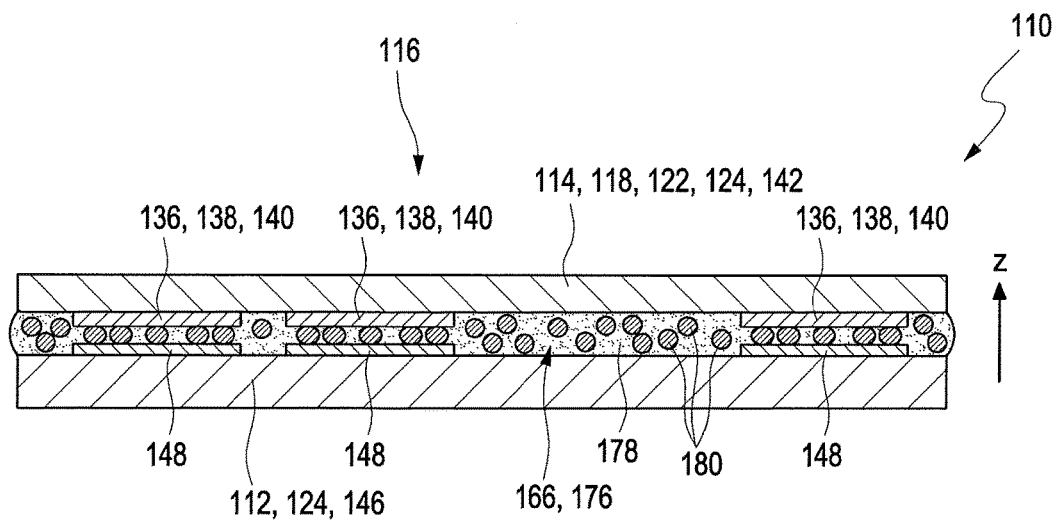
FIGS. 5 and 6 show further details of an electric interconnection in the overlap area, generated by using an anisotropic conductive adhesive.
Figure 6:
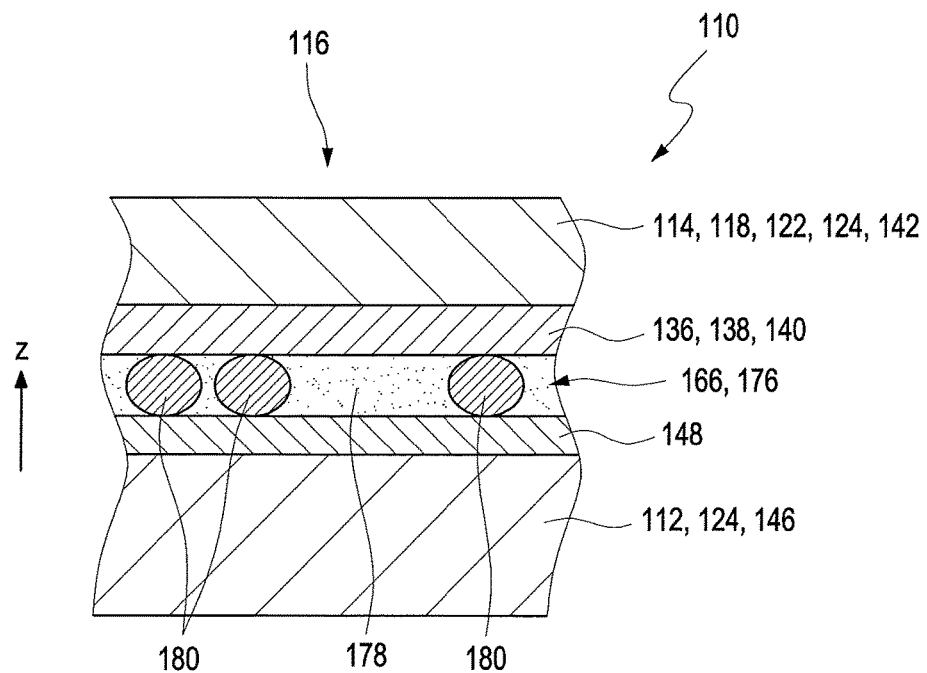

As depicted in FIG. 1, the connector part 142 of the sensor unit 114 is mechanically and electrically connected to the evaluation unit substrate 146. In FIG. 2, the connector part 142 is embodied as a connector having a plurality of separate fingers 164. However, other embodiments are feasible, such as embodiments having only one end of the connector part 140, wherein all connector portions 140 are located within the same end of the connector part 142. With reference to FIGS. 4, 5 and 6, a potential embodiment of a process for connecting the sensor unit 114 to the evaluation unit 112 will be disclosed in further detail.

Thus, firstly, as depicted in FIG. 4, an anisotropic conductive adhesive 166 is applied in between the connector portions 140 and the electric contact pads 148, such as by large-area application of the anisotropic conductive adhesive 166 onto the electric contact pads 148. Simultaneously or subsequently, the connector part 142 is aligned to the evaluation unit substrate 146, such that the connector portions 140 are aligned to corresponding electric contact pads 148. Thus, as an example, in the embodiment of FIG. 2 having a plurality of fingers 164, each of the fingers 164 may be aligned to the respective electric contact pad 148. However, other types of alignment are possible.

Subsequently, heat 168 and/or pressure 170, both symbolically denoted by arrows in FIG. 4, are applied to the sensor unit substrate 122 in the region of the connector portions 140 and/or to the evaluation unit substrate 146 in the region of the electric contact pads 148. For this purpose, one or more appropriate stamps may be used, for both applying heat 168 and/or pressure 170. As outlined above, other types of bonding may be performed, such as by applying pressure 170 and radiation.

As can further be seen in FIG. 4, preferably, an excess amount of anisotropic conductive adhesive 166 may be applied, such that, along one or more edges 172 of the evaluation unit substrate 146 and/or the sensor unit substrate 122 one or more beads 174 are formed, thereby improving a mechanical stability of the bonded joint.

When applying the pressure 170, the anisotropic conductive adhesive 166 is compressed in a direction of application of the pressure 170 (direction of the arrows in FIG. 4), thereby forming a thin film or layer 176 having anisotropic conductive properties. Thus, an electric conductivity is provided in a direction perpendicular to the substrates 122, 146 in FIG. 4, i.e. a direction denoted by z in FIG. 4, which is a direction from the electric contact pads 148 to the respective connector portions 140 or vice versa, wherein, in any direction perpendicular to direction z, an electric insulation is provided.

In FIGS. 5 and 6, details of the connection region 116 with the anisotropic conductive adhesive 166 applied are depicted. Therein, a setup slightly deviating from the setup of FIG. 2, having a plurality of fingers 164, is depicted. Thus, FIG. 5 shows a setup in which all connector portions 140 of the sensor unit 114 are located on the same end of the connector substrate 124. However, other embodiments are feasible.

As depicted in FIG. 5, the connector portions 140 are aligned facing the respective counterparts on the side of the electric contact pads 148, such that each connector portion faces one respective electric contact pad. Thus, FIG. 5 shows a cross-sectional view of the connection region 116, perpendicular to the extension of the conductive paths 136, whereas FIG. 6 shows a cross-sectional view more in detail, indicating the deformation of the circular cross section of the conducting particles 180 into an almost elliptic shape.

In between the connector portions 140 and the electric contact pads 148, the anisotropic conductive adhesive 166 is comprised. As depicted in FIGS. 5 and 6, this anisotropic conductive adhesive 166 comprises at least one matrix material 178, which, preferably, has electrically insulating properties and, which, preferably, is curable, such as by applying heat 168 (thermosetting material) and/or by photochemical curing (such as by applying radiation) and/or by chemical curing. Thus, as an example, the matrix material 178 may comprise at least one epoxy resin. Matrix material 178 may be formed by a one-component matrix material 178 and/or a multi-component matrix material 178, such as by providing a plurality of components capable of performing a chemical cross-linking reaction for curing purposes.

As depicted in FIGS. 5 and 6, the anisotropic conductive adhesive 166 further may comprise a plurality of conductive particles 180. As an example, conductive particles having an average particle size of 3 µm may be used. Other particle sizes are possible. As further indicated in FIGS. 5 and 6, when pressure 170 is applied (as depicted e.g. in FIG. 4), the anisotropic conductive adhesive 166 is compressed to form a layer 176 of the anisotropic conductive adhesive. Specifically in the region of the connector portions 140 and/or the electric contact pads 148, specifically in between these connector portions 140 and electric contact pads 148, the layer 176 may have a layer thickness which is smaller than the size of the pristine conductive particles 180. Due to the pressure 170 applied the conductive particles 180 may be deformed from a circular cross section to an almost elliptic one. Also, the conducting materials of the contact pads 148 respective the connector portions 140 may be deformed slightly. Thereby, an electrical connection may be provided in the z-direction in between the connector portions 140 and their corresponding electric contact pads 148, via the conductive particles 180, whereas an electrical insulation is provided in any direction perpendicular to the z-direction. Thereby, the layer 176 formed by the compressed anisotropic conductive adhesive 166 has anisotropic conductive properties.

In the following, exemplary embodiments of experimental setups for testing the mechanical/electrical interconnection of the evaluation unit 112 and the sensor unit 114 according to the present invention are disclosed.

Exemplary Embodiment 1: Manufacturing of a Sensor Unit Having Conductive Paths Made of Gold As a baseline for comparing devices having electrically conductive organic materials and devices having other types of electrically conductive materials, a dummy sensor unit 114 was manufactured by using conductive paths made of gold as an electrically conductive material instead of electrically conductive organic materials. As a connector substrate 124, a white PET foil having a thickness of 350 µm was used, obtained by Mitsubishi Polyester Film GmbH, Wiesbaden, Germany. Thereon, conductive paths 136 were deposited by using gold as a conductive metal, having a thickness of 100 nm. By using a laser ablation technique (ultraviolet laser) a part of the gold layer is removed, in order to pattern the conductive paths, the sensor electrodes 126 and the connector portions 140. Subsequently, by using a $CO_2$ laser, single sensor units 114 are cut from the PET foil.

Exemplary Embodiment 2: Manufacturing of a Sensor Unit Having Conductive Paths Made of PEDOT:PSS Further, a sensor unit 114 having conductive paths 136 made of an electrically conductive organic material, specifically an electrically conductive polymer, was manufactured, by using PEDOT:PSS as the electrically conductive organic material. For this purpose, on to a white PET foil having a thickness of 350 µm, provided by Mitsubishi Polyester Film GmbH, Wiesbaden, Germany, a dispersion of PEDOT:PSS (Clevios SV4, Heraeus, Leverkusen, Germany) was applied by a large-area coating using a doctor blading technique. Thereby, after drying at 100° C. for 60 minutes at ambient pressure, a dry layer thickness of PEDOT:PSS of 2 µm was generated. By using a $CO_2$ laser, single conductive paths were patterned in the PEDOT:PSS layer, including corresponding connector portions and having conductive pads for sensor electrodes 126. The geometry of the pattern corresponded to the geometry of exemplary embodiment 1 above. By using a $CO_2$ laser, single sensor units 114 were cut from the PET foil.

It should be noted that, in exemplary embodiments 1 and 2, the sensor units manufactured were used as dummy elements and, thus, were not fully completed by appropriate subsequent steps. Thus, as an example, no detector substance 130 was added to the sensor electrodes 126. Thus, when referring to the elements manufactured according to exemplary embodiments 1 and 2 above as sensor units, it should be noted that these sensor units were used as dummy sensor units only, for the purpose of testing the mechanical and/or electrical interconnection by using the method according to the present invention, without providing the actual capability of sensing an analyte.

Exemplary Embodiment 3: Bonding the Sensor Unit According to Exemplary Embodiment 1 Above to a Printed Circuit Board In this experiment, a connector part of the sensor unit 114 according to exemplary embodiment 1 above was glued to appropriate electric contact pads of a printed circuit board. For this purpose, a printed circuit board having a connector substrate made of FR4 was used. Thereon, electric contact pads made of gold by galvanic deposition were applied, having a mirror-symmetric symmetry to the connector portions of the sensor units. The connector portions were aligned to the electric contact pads, with 4 µl of Elecolit® 3061, obtained by Panacol-Elosol GmbH, Steinbach, Germany, applied in between the connector portions and the electric contact pads. An area of overlap was chosen to be approximately 5×3 mm$^2$. A heated stamp having a temperature of approximately 170° C. was pressed on to the backside of the PET foil and pressed with a force of approximately 40 N for approximately 45 s. Therein, as opposed to the recommended parameters provided by the manufacturer of the anisotropic conductive adhesive (Elecolit® 3061), temperature and pressure time were increased, since PET foils turned out to have a lower thermal conductivity as compared to silicon.

After cooling down the device, a rigid interconnection between the sensor unit and the evaluation unit was detected. In between the conductive paths of the sensor unit and corresponding electric contact pads on the evaluation unit substrate, a low-resistance electrical contact was detected. Between neighboring conductive paths, an electric insulation was detected having a resistance of more than $10^9 \Omega$.

Exemplary Embodiment 4: Bonding of Sensor Units Having PEDOT:PSS to an Evaluation Unit Substrate In analogy to exemplary embodiment 3 above, the sensor unit of exemplary embodiment 2 was glued to a printed circuit board as described above in exemplary embodiment 3. Similar results as disclosed in exemplary embodiment 3 were obtained.

Exemplary Embodiment 5: Bonding a Sensor Unit Having PEDOT:PSS to a Sensor Unit Having Gold Conductive Paths In a further exemplary embodiment, the sensor unit of exemplary embodiment 1 was glued to the sensor unit of exemplary embodiment 2, by gluing the connector portions of the sensor unit according to exemplary embodiment 1 to corresponding connector portions of the sensor unit according to exemplary embodiment 2, by using the gluing process as disclosed in exemplary embodiment 3 above. Therein, when applying the anisotropic conductive adhesive, care was taken to provide an excessive amount of anisotropic conductive adhesive, in order to create the beads as disclosed above.

After cooling down the setup, a rigid mechanical interconnection between the two sensor units was detected. Further, between corresponding conductive paths of the sensor unit, a low-resistance electrical contact was detected. Between neighboring conductive paths, no contact or an insulation was detected, having a resistance of more than $10^9 \Omega$.

Exemplary Embodiment 6: Sterilization of the Setup of Exemplary Embodiment 5

Further, the setup obtained according to exemplary embodiment 5, having a sensor unit comprising conductive paths made of gold and a sensor unit comprising conductive paths made of PEDOT:PSS, was sterilized by using a radiation sterilization. For this purpose, an electron beam sterilization providing a dose of 25 kGy was applied. The sterilization was performed at BGS BETA-GAMMA-SERVICE GmbH, Bruchsal, Germany.

It was found that, after sterilization, both the electrical and the mechanical properties of the setup did not substantially differ from the results as disclosed in exemplary embodiment 5 above. Thus, the sterilization by radiation obviously does not lead to a deterioration of the mechanical and/or electrical properties.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

LIST OF REFERENCE NUMBERS 110 device for monitoring at least one body function
112 evaluation unit
114 sensor unit
116 connection region
118 implantable sensor unit
120 implantable portion
122 sensor unit substrate
124 connector substrate
126 sensor electrode
128 working electrode
130 detector substance
132 counter electrode
134 reference electrode
136 conductive path
138 electrically conductive material
140 connector portion
142 connector part
144 insulating layer
146 evaluation unit substrate
148 electric contact pad
150 electronic device 152 lead
154 casing
156 bottom part
158 top part
160 inner space
162 opening
164 fingers
166 anisotropic conductive adhesive
168 heat
170 pressure
172 edge
174 bead
176 layer
178 matrix material
180 conductive particles

The invention claimed is:

1. A method for manufacturing a device for monitoring at least one body function of a user, wherein the device comprises at least one evaluation unit and at least one sensor unit, wherein the method comprises the following steps:
   a) a step of providing the evaluation unit, wherein the evaluation unit has at least one electric contact pad applied to at least one evaluation unit substrate, wherein the electric contact pad is electrically connected to at least one electronic device of the evaluation unit;
   b) a step of providing the sensor unit, wherein the sensor unit comprises at least one connector part, wherein the connector part comprises at least one connector substrate and at least one conductive path applied to the connector substrate, wherein the conductive path comprises at least one electrically conductive material, wherein the electrically conductive material comprises an electrically conductive polymer, and wherein the conductive path has at least one connector portion;
   c) a preparation step, wherein the connector portion is aligned next to the electric contact pad such that the connector portion faces the electric contact pad, wherein at least one anisotropic conductive adhesive is provided in between the electric contact pad and the connector portion, wherein the anisotropic conductive adhesive is applied in an amorphous form; and
   d) a bonding step, wherein the evaluation unit substrate and the connector substrate are pressed together, wherein the electric contact pad and the connector portion are pressed together, and wherein an electric connection of the electric contact pad and the connector portion is created via the anisotropic conductive adhesive, wherein in the preparation step, the anisotropic conductive adhesive is applied excessively such that, after performing the bonding step, a bead of excess anisotropic conductive adhesive is formed at at least one edge of at least one of the evaluation unit substrate and the connector substrate.

2. The method of claim 1 wherein the sensor unit comprises at least one implantable sensor unit and wherein the implantable sensor unit comprises at least one implantable portion adapted for implantation into a body tissue of the user.

3. The method of claim 1 wherein the sensor unit comprises at least two sensor electrodes and wherein the at least two sensor electrodes are adapted for electrochemically determining at least one concentration of an analyte in a body tissue or body fluid of the user.

4. The method of claim 3 wherein the sensor electrodes comprise at least one working electrode, the working electrode having at least one detector substance adapted for performing at least one electrochemical reaction in the presence of the analyte.

5. The method of claim 1 wherein the step of providing the sensor unit comprises at least one substep of structuring the conductive path.

6. The method of claim 1 wherein the connector substrate comprises at least one plastic substrate.

7. The method of claim 1 wherein step b) comprises providing a plurality of sensor units on a common substrate and at least one cutting step wherein the sensor units are cut from the common substrate.

8. The method of claim 1 wherein the connector substrate is flexible or deformable.

9. The method of claim 1 wherein the sensor unit comprises a plurality of conductive paths, each conductive path having at least one connector portion, wherein the evaluation unit comprises a plurality of electric contact pads, and wherein in the preparation step, each connector portion is aligned to a corresponding electric contact pad.

10. The method of claim 1 wherein in the bonding step, one or more of pressure, heat and radiation are applied.

11. The method of claim 1 wherein after performing the bonding step, the device is at least partially sterilized by radiation sterilization.

* * * * *